United States Patent
Huelskamp

(10) Patent No.: US 7,955,268 B2
(45) Date of Patent: Jun. 7, 2011

(54) MULTIPLE SENSOR DEPLOYMENT

(75) Inventor: Paul J. Huelskamp, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 156 days.

(21) Appl. No.: 11/781,100

(22) Filed: Jul. 20, 2007

(65) Prior Publication Data
US 2008/0021333 A1    Jan. 24, 2008

Related U.S. Application Data

(60) Provisional application No. 60/820,050, filed on Jul. 21, 2006, provisional application No. 60/820,059, filed on Jul. 21, 2006.

(51) Int. Cl.
*A61B 5/02* (2006.01)
(52) U.S. Cl. ...................................................... 600/486
(58) Field of Classification Search .................. 600/485, 600/486
See application file for complete search history.

(56) References Cited

U.S. PATENT DOCUMENTS

| | | | |
|---|---|---|---|
| 3,310,885 A | 3/1967 | Alderson | |
| 3,320,946 A | 5/1967 | Dethloff et al. | |
| 3,536,836 A | 10/1970 | Pfeiffer | |
| 3,568,661 A | 3/1971 | Franklin | |
| 3,672,352 A | 6/1972 | Summers | |
| 3,692,027 A | 9/1972 | Ellinwood | |
| 3,757,770 A | 9/1973 | Brayshaw et al. | |
| 3,794,840 A | 2/1974 | Scott | |
| 3,868,578 A | 2/1975 | Oldham | |
| 3,943,915 A | 3/1976 | Severson | |
| 4,003,379 A | 1/1977 | Ellinwood | |
| 4,041,954 A | 8/1977 | Ohara | |
| 4,127,110 A | 11/1978 | Bullara | |
| 4,146,029 A | 3/1979 | Ellinwood | |
| 4,223,801 A | 9/1980 | Carlson | |
| 4,227,407 A | 10/1980 | Drost | |

(Continued)

FOREIGN PATENT DOCUMENTS

EP    0897690    2/1999

(Continued)

OTHER PUBLICATIONS

International Search Report and Written Opinion of international application No. PCT/US2007/074020, mailed Feb. 20, 2008, 15 pp.

(Continued)

*Primary Examiner* — Patricia C Mallari
*Assistant Examiner* — Christian Jang
(74) *Attorney, Agent, or Firm* — Faegre & Benson LLP

(57) ABSTRACT

A method of measuring pressure within the human body including implanting a pressure sensing assembly having a flexible structure and first and second sensor elements having self-contained power supplies coupled to the flexible structure. Periodic data collection events are performed to collect data from the sensor elements. A data collection event includes a request for data from a remote communication device, a transfer of sensor data to the remote communication device and a processing of the sensor data. The invention also includes a sensor assembly for implantation into a human body. The sensor assembly includes a first sensor having a self-contained power supply, a sensing element and an integral communication device capable of communicating with a remote communication device. The sensor assembly also includes a second sensor and a flexible structure to which the first and second sensor are attached.

19 Claims, 7 Drawing Sheets

U.S. PATENT DOCUMENTS

| | | |
|---|---|---|
| 4,237,900 A | 12/1980 | Schulman et al. |
| 4,281,664 A | 8/1981 | Duggen |
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,583,553 A | 4/1986 | Shah et al. |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,716,903 A | 1/1988 | Hansen et al. |
| 4,719,921 A | 1/1988 | Chirife |
| 4,726,380 A | 2/1988 | Vollmann et al. |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,825 A | 12/1988 | Benjamin et al. |
| 4,809,697 A | 3/1989 | Causey, III et al. |
| 4,814,974 A | 3/1989 | Narayanan et al. |
| 4,845,503 A | 7/1989 | Adam et al. |
| 4,846,191 A | 7/1989 | Brockway et al. |
| 4,854,327 A | 8/1989 | Kunig |
| 4,899,752 A | 2/1990 | Cohen |
| 4,909,259 A | 3/1990 | Tehrani |
| 4,920,489 A | 4/1990 | Hubelbank et al. |
| 4,945,477 A | 7/1990 | Edwards |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,002,062 A | 3/1991 | Suzuki |
| 5,003,976 A | 4/1991 | Alt |
| 5,007,431 A | 4/1991 | Donehoo, III |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,052,399 A | 10/1991 | Olive et al. |
| 5,113,859 A | 5/1992 | Funke |
| 5,139,020 A | 8/1992 | Koestner et al. |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,183,051 A | 2/1993 | Kraidin et al. |
| 5,188,106 A | 2/1993 | Nappholz et al. |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,215,098 A | 6/1993 | Steinhaus et al. |
| 5,217,021 A | 6/1993 | Steinhaus et al. |
| 5,246,008 A | 9/1993 | Mueller |
| 5,263,486 A | 11/1993 | Jeffreys |
| 5,265,615 A | 11/1993 | Frank et al. |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,309,919 A | 5/1994 | Snell et al. |
| 5,312,446 A | 5/1994 | Holschbach et al. |
| 5,313,953 A | 5/1994 | Yomtov et al. |
| 5,314,457 A | 5/1994 | Jeutter et al. |
| 5,329,459 A | 7/1994 | Kaufman et al. |
| 5,330,505 A | 7/1994 | Cohen |
| 5,331,966 A | 7/1994 | Bennett et al. |
| 5,339,051 A | 8/1994 | Koehler et al. |
| 5,354,316 A | 10/1994 | Keimel |
| 5,360,440 A | 11/1994 | Andersen |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,400,793 A | 3/1995 | Wesseling |
| 5,411,535 A | 5/1995 | Fujii et al. |
| 5,411,551 A | 5/1995 | Winston et al. |
| 5,417,717 A | 5/1995 | Salo et al. |
| 5,423,323 A | 6/1995 | Orth |
| 5,423,334 A | 6/1995 | Jordan |
| 5,438,990 A | 8/1995 | Wahlstrand et al. |
| 5,442,351 A | 8/1995 | Horspool et al. |
| 5,445,608 A | 8/1995 | Chen et al. |
| 5,454,838 A | 10/1995 | Vallana et al. |
| 5,458,627 A | 10/1995 | Baranowski, Jr. et al. |
| 5,469,859 A | 11/1995 | Tsoglin et al. |
| 5,476,488 A | 12/1995 | Morgan et al. |
| 5,488,954 A | 2/1996 | Sleva et al. |
| 5,490,962 A | 2/1996 | Cima et al. |
| 5,507,780 A | 4/1996 | Finch |
| 5,509,424 A | 4/1996 | Al Ali |
| 5,518,001 A | 5/1996 | Snell |
| 5,528,067 A | 6/1996 | Farb |
| 5,535,752 A | 7/1996 | Halperin et al. |
| 5,545,186 A | 8/1996 | Olson et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,603,331 A | 2/1997 | Heemels et al. |
| 5,604,531 A | 2/1997 | Iddan et al. |
| 5,619,997 A | 4/1997 | Kaplan |
| 5,623,935 A | 4/1997 | Faisandier |
| 5,626,630 A | 5/1997 | Markowitz et al. |
| 5,628,782 A | 5/1997 | Myers |
| 5,642,731 A | 7/1997 | Kehr |
| 5,643,327 A | 7/1997 | Dawson et al. |
| 5,647,369 A | 7/1997 | Petrucelli et al. |
| 5,656,428 A | 8/1997 | McAllister et al. |
| 5,704,352 A | 1/1998 | Tremblay et al. |
| 5,705,753 A | 1/1998 | Hastings et al. |
| 5,709,216 A | 1/1998 | Woodson, III |
| 5,728,281 A | 3/1998 | Holstrom et al. |
| 5,729,129 A | 3/1998 | Acker |
| 5,732,708 A | 3/1998 | Nau et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,772,999 A | 6/1998 | Greenblatt et al. |
| 5,776,168 A | 7/1998 | Gunderson |
| 5,776,324 A | 7/1998 | Usala |
| 5,779,634 A | 7/1998 | Ema et al. |
| 5,785,660 A | 7/1998 | van Lake et al. |
| 5,792,195 A | 8/1998 | Carlson et al. |
| 5,796,827 A | 8/1998 | Coppersmith et al. |
| 5,797,395 A | 8/1998 | Martin |
| 5,797,898 A | 8/1998 | Santini, Jr. et al. |
| 5,800,478 A | 9/1998 | Chen et al. |
| 5,804,258 A | 9/1998 | Lohwasser et al. |
| 5,807,258 A | 9/1998 | Cimochowski et al. |
| 5,807,395 A | 9/1998 | Mulier et al. |
| 5,807,397 A | 9/1998 | Barreras |
| 5,810,009 A | 9/1998 | Mine et al. |

| | | |
|---|---|---|
| 5,810,735 A | 9/1998 | Halperin et al. |
| 5,819,740 A | 10/1998 | Muhlenberg et al. |
| 5,832,924 A | 11/1998 | Archibald et al. |
| 5,833,603 A | 11/1998 | Kovacs et al. |
| 5,833,715 A | 11/1998 | Vachon et al. |
| 5,835,455 A | 11/1998 | Hanson et al. |
| 5,836,300 A | 11/1998 | Mault |
| 5,836,889 A | 11/1998 | Wyborny et al. |
| 5,836,982 A | 11/1998 | Muhlenberg et al. |
| 5,843,089 A | 12/1998 | Sahatjian et al. |
| 5,843,135 A | 12/1998 | Weijand et al. |
| 5,855,609 A | 1/1999 | Knapp |
| 5,856,722 A | 1/1999 | Haronian et al. |
| 5,868,673 A | 2/1999 | Vesely |
| 5,873,835 A | 2/1999 | Hastings et al. |
| 5,873,904 A | 2/1999 | Ragheb et al. |
| 5,880,661 A | 3/1999 | Davidson et al. |
| 5,886,267 A | 3/1999 | Ortiz |
| 5,891,180 A | 4/1999 | Greeninger et al. |
| 5,904,708 A | 5/1999 | Goedeke et al. |
| 5,908,392 A | 6/1999 | Wilson et al. |
| 5,911,685 A | 6/1999 | Siess et al. |
| 5,919,221 A | 7/1999 | Miesel |
| 5,935,081 A | 8/1999 | Kadhiresan |
| 5,938,903 A | 8/1999 | Broderick |
| 5,941,249 A | 8/1999 | Maynard |
| 5,951,458 A | 9/1999 | Hastings et al. |
| 5,954,641 A | 9/1999 | Kehr et al. |
| 5,957,950 A | 9/1999 | Mockros et al. |
| 5,967,986 A | 10/1999 | Cimochowski et al. |
| 5,976,169 A | 11/1999 | Imran |
| 5,979,898 A | 11/1999 | Pan |
| 5,980,554 A | 11/1999 | Lenker et al. |
| 6,002,963 A | 12/1999 | Mouchawar et al. |
| 6,009,472 A | 12/1999 | Boudou et al. |
| 6,021,347 A | 2/2000 | Herbst et al. |
| 6,023,641 A | 2/2000 | Thompson |
| 6,024,704 A | 2/2000 | Meador et al. |
| 6,050,951 A | 4/2000 | Friedman et al. |
| 6,053,873 A | 4/2000 | Govari et al. |
| 6,080,190 A | 6/2000 | Schwartz |
| 6,083,248 A | 7/2000 | Thompson |
| 6,112,116 A | 8/2000 | Fischell et al. |
| 6,123,861 A | 9/2000 | Santini, Jr. et al. |
| 6,140,740 A | 10/2000 | Porat et al. |
| 6,141,588 A * | 10/2000 | Cox et al. .................... 607/9 |
| 6,152,885 A | 11/2000 | Taepke |
| 6,155,267 A | 12/2000 | Nelson |
| 6,161,032 A | 12/2000 | Acker |
| 6,162,238 A | 12/2000 | Kaplan et al. |
| 6,164,284 A | 12/2000 | Schulman et al. |
| 6,170,488 B1 | 1/2001 | Spillman, Jr. et al. |
| 6,171,252 B1 | 1/2001 | Roberts |
| 6,179,767 B1 | 1/2001 | Ziegler et al. |
| 6,185,452 B1 | 2/2001 | Schulman et al. |
| 6,185,455 B1 | 2/2001 | Loeb et al. |
| 6,185,457 B1 | 2/2001 | Kroll et al. |
| 6,198,965 B1 | 3/2001 | Penner et al. |
| 6,200,265 B1 | 3/2001 | Walsh et al. |
| 6,201,991 B1 | 3/2001 | Chekanov |
| 6,206,914 B1 | 3/2001 | Soykan et al. |
| 6,227,078 B1 | 5/2001 | Lemmo, Jr. |
| 6,234,973 B1 | 5/2001 | Meador et al. |
| 6,236,889 B1 | 5/2001 | Soykan et al. |
| 6,237,398 B1 | 5/2001 | Porat et al. |
| 6,239,724 B1 | 5/2001 | Doron et al. |
| 6,248,080 B1 | 6/2001 | Miesel et al. |
| 6,253,260 B1 | 6/2001 | Beardsley et al. |
| 6,256,538 B1 | 7/2001 | Ekwall |
| 6,266,567 B1 | 7/2001 | Ishikawa et al. |
| 6,273,904 B1 | 8/2001 | Chen et al. |
| 6,277,078 B1 | 8/2001 | Porat et al. |
| 6,278,894 B1 | 8/2001 | Salo et al. |
| 6,287,332 B1 | 9/2001 | Bolz et al. |
| 6,305,381 B1 | 10/2001 | Weijand et al. |
| 6,308,099 B1 | 10/2001 | Fox et al. |
| 6,314,323 B1 | 11/2001 | Ekwall |
| 6,330,957 B1 | 12/2001 | Bell-Greenstreet |
| 6,331,163 B1 | 12/2001 | Kaplan |
| 6,347,245 B1 | 2/2002 | Lee et al. |
| 6,366,808 B1 | 4/2002 | Schroeppel et al. |
| 6,368,275 B1 | 4/2002 | Sliwa et al. |
| 6,397,661 B1 | 6/2002 | Grimes et al. |
| 6,409,674 B1 | 6/2002 | Brockway et al. |
| 6,409,675 B1 | 6/2002 | Turcott |
| 6,411,850 B1 | 6/2002 | Kay et al. |
| 6,416,474 B1 | 7/2002 | Penner et al. |
| 6,421,565 B1 | 7/2002 | Hemmingsson |
| 6,431,175 B1 | 8/2002 | Penner et al. |
| 6,432,050 B1 | 8/2002 | Porat et al. |
| 6,438,408 B1 | 8/2002 | Mulligan et al. |
| 6,441,747 B1 | 8/2002 | Khair et al. |
| 6,442,413 B1 | 8/2002 | Silver |
| 6,445,953 B1 | 9/2002 | Bulkes et al. |
| 6,456,883 B1 | 9/2002 | Torgerson et al. |
| 6,471,645 B1 | 10/2002 | Warkentin et al. |
| 6,472,991 B1 | 10/2002 | Schulman et al. |
| 6,475,147 B1 | 11/2002 | Yost et al. |
| 6,475,170 B1 | 11/2002 | Doron et al. |
| 6,486,588 B2 | 11/2002 | Doron et al. |
| 6,504,286 B1 | 1/2003 | Porat et al. |
| 6,522,914 B1 | 2/2003 | Huvelle et al. |
| 6,526,314 B1 | 2/2003 | Eberle et al. |
| 6,567,700 B1 | 5/2003 | Turcott et al. |
| 6,574,510 B2 | 6/2003 | Von Arx et al. |
| 6,580,946 B2 | 6/2003 | Struble |
| 6,584,349 B1 | 6/2003 | Sage et al. |
| 6,584,354 B1 | 6/2003 | Mann et al. |
| 6,585,764 B2 | 7/2003 | Wright et al. |
| 6,589,187 B1 | 7/2003 | Dirnberger et al. |
| 6,599,242 B1 | 7/2003 | Splett et al. |
| 6,604,000 B2 | 8/2003 | Lu |
| 6,607,485 B2 | 8/2003 | Bardy |
| 6,609,023 B1 | 8/2003 | Fischell et al. |
| 6,615,083 B2 | 9/2003 | Kupper |
| 6,622,049 B2 | 9/2003 | Penner et al. |
| 6,622,050 B2 | 9/2003 | Thompson |
| 6,628,985 B2 | 9/2003 | Sweeney et al. |
| 6,628,989 B1 | 9/2003 | Penner et al. |
| 6,644,322 B2 | 11/2003 | Webb |
| 6,650,939 B2 | 11/2003 | Taepke, II et al. |
| 6,654,638 B1 | 11/2003 | Sweeney |
| 6,660,034 B1 | 12/2003 | Mandrusov et al. |
| 6,675,049 B2 | 1/2004 | Thompson et al. |
| 6,682,985 B2 | 1/2004 | Yuzuriha et al. |
| 6,699,186 B1 | 3/2004 | Wolinsky et al. |
| 6,708,061 B2 | 3/2004 | Salo et al. |
| 6,708,065 B2 | 3/2004 | Von Arx et al. |
| 6,719,689 B2 | 4/2004 | Munneke et al. |
| 6,720,709 B2 | 4/2004 | Porat et al. |
| 6,720,887 B1 | 4/2004 | Zunti |
| 6,733,447 B2 | 5/2004 | Lai et al. |
| 6,738,667 B2 | 5/2004 | Deno et al. |
| 6,738,671 B2 | 5/2004 | Christophersom et al. |
| 6,743,173 B2 | 6/2004 | Penner et al. |
| 6,754,795 B2 | 6/2004 | Chen et al. |
| 6,758,822 B2 | 7/2004 | Romano |
| 6,764,446 B2 | 7/2004 | Wolinsky et al. |
| 6,778,859 B2 | 8/2004 | Graindorge |
| 6,782,810 B2 | 8/2004 | Vilo |
| 6,792,308 B2 | 9/2004 | Corbucci |
| 6,792,311 B2 | 9/2004 | Fox et al. |
| 6,805,667 B2 | 10/2004 | Christopherson et al. |
| 6,823,210 B2 | 11/2004 | Eberle et al. |
| 6,824,512 B2 | 11/2004 | Warkentin et al. |
| 6,832,112 B1 | 12/2004 | Bornzin |
| 6,840,956 B1 | 1/2005 | Wolinsky et al. |
| 6,859,665 B2 | 2/2005 | Ding et al. |
| 6,865,419 B2 | 3/2005 | Mulligan et al. |
| 6,868,346 B2 | 3/2005 | Larson et al. |
| 6,869,404 B2 | 3/2005 | Schulhauser et al. |
| 6,871,088 B2 | 3/2005 | Chinchoy |
| 6,885,889 B2 | 4/2005 | Chinchoy |
| 6,889,086 B2 | 5/2005 | Mass et al. |
| 6,910,084 B2 | 6/2005 | Augustijn et al. |
| 6,915,162 B2 | 7/2005 | Noren et al. |
| 6,926,670 B2 | 8/2005 | Rich et al. |
| 6,937,900 B1 | 8/2005 | Pianca et al. |

| | | |
|---|---|---|
| 6,949,075 B2 | 9/2005 | Hatlesad et al. |
| 6,961,448 B2 | 11/2005 | Nichols et al. |
| 6,961,617 B1 | 11/2005 | Snell |
| 6,970,742 B2 | 11/2005 | Mann et al. |
| 6,978,182 B2 | 12/2005 | Mazar et al. |
| 6,985,773 B2 | 1/2006 | Von Arx et al. |
| 6,993,393 B2 | 1/2006 | Von Arx et al. |
| 7,003,350 B2 | 2/2006 | Denker et al. |
| 7,016,721 B2 | 3/2006 | Lee et al. |
| 7,024,248 B2 | 4/2006 | Penner et al. |
| 7,027,872 B2 | 4/2006 | Thompson |
| 7,035,684 B2 | 4/2006 | Lee |
| 7,047,065 B2 * | 5/2006 | Kalgren et al. ............ 600/510 |
| 7,048,691 B2 | 5/2006 | Miele et al. |
| 7,060,030 B2 | 6/2006 | Von Arx et al. |
| 7,088,254 B2 | 8/2006 | Liebenow |
| 7,127,290 B2 | 10/2006 | Girouard et al. |
| 7,130,678 B2 | 10/2006 | Ritscher et al. |
| 7,130,681 B2 | 10/2006 | Gebhardt et al. |
| 7,136,703 B1 | 11/2006 | Cappa et al. |
| 7,160,252 B2 | 1/2007 | Cho et al. |
| 7,181,268 B2 | 2/2007 | Sheldon et al. |
| 7,195,594 B2 | 3/2007 | Eigler et al. |
| 7,198,603 B2 | 4/2007 | Penner et al. |
| 7,200,439 B2 | 4/2007 | Zdeblick et al. |
| 7,203,545 B2 | 4/2007 | Schmitt et al. |
| 7,204,798 B2 | 4/2007 | Zdeblick et al. |
| 7,209,790 B2 | 4/2007 | Thompson et al. |
| 7,212,861 B1 | 5/2007 | Park et al |
| 7,225,030 B2 | 5/2007 | Kroll et al. |
| 7,248,923 B2 | 7/2007 | Maile et al. |
| 7,273,457 B2 | 9/2007 | Penner |
| 7,294,105 B1 * | 11/2007 | Islam ............................ 600/300 |
| 7,335,161 B2 | 2/2008 | Von Arx et al. |
| 7,392,090 B2 | 6/2008 | Sweeney et al. |
| 7,742,815 B2 | 6/2010 | Sale et al. |
| 2001/0051766 A1 * | 12/2001 | Gazdzinski ............... 600/309 |
| 2002/0023123 A1 | 2/2002 | Madison |
| 2002/0042561 A1 | 4/2002 | Schulman et al. |
| 2002/0045812 A1 | 4/2002 | Ben-Haim et al. |
| 2002/0045836 A1 | 4/2002 | Alkawwas |
| 2002/0062086 A1 | 5/2002 | Miele et al. |
| 2002/0077553 A1 | 6/2002 | Govari et al. |
| 2002/0077556 A1 | 6/2002 | Schwartz |
| 2002/0120204 A1 | 8/2002 | Pfeiffer et al. |
| 2002/0126036 A1 * | 9/2002 | Flaherty et al. ............... 341/176 |
| 2002/0128546 A1 | 9/2002 | Silver |
| 2002/0138009 A1 | 9/2002 | Brockway et al. |
| 2002/0147406 A1 | 10/2002 | von Segesser |
| 2002/0151770 A1 | 10/2002 | Noll, III et al. |
| 2002/0183628 A1 * | 12/2002 | Reich et al. ................. 600/486 |
| 2002/0183791 A1 | 12/2002 | Denker et al. |
| 2002/0188323 A1 | 12/2002 | Penner et al. |
| 2003/0004562 A1 * | 1/2003 | DiCarlo ....................... 623/1.13 |
| 2003/0009093 A1 | 1/2003 | Silver |
| 2003/0009204 A1 | 1/2003 | Amundson et al. |
| 2003/0045805 A1 | 3/2003 | Sheldon et al. |
| 2003/0076082 A1 | 4/2003 | Morgan et al. |
| 2003/0100839 A1 | 5/2003 | Cohen et al. |
| 2003/0114897 A1 | 6/2003 | Von Arx et al. |
| 2003/0125613 A1 | 7/2003 | Enegren et al. |
| 2003/0136417 A1 | 7/2003 | Fonseca et al. |
| 2003/0139677 A1 | 7/2003 | Fonseca et al. |
| 2003/0158584 A1 | 8/2003 | Cates et al. |
| 2003/0181794 A1 | 9/2003 | Rini et al. |
| 2003/0189488 A1 | 10/2003 | Forcier et al. |
| 2003/0191383 A1 | 10/2003 | Ben-Haim et al. |
| 2003/0199779 A1 | 10/2003 | Muhlenberg |
| 2004/0032187 A1 | 2/2004 | Penner et al. |
| 2004/0044393 A1 | 3/2004 | Yarden et al. |
| 2004/0064133 A1 | 4/2004 | Miller et al. |
| 2004/0077937 A1 | 4/2004 | Yarden |
| 2004/0122484 A1 | 6/2004 | Hatlestad et al. |
| 2004/0122486 A1 | 6/2004 | Stahmann et al. |
| 2004/0152999 A1 | 8/2004 | Cohen et al. |
| 2004/0158163 A1 | 8/2004 | Cohen et al. |
| 2004/0167416 A1 | 8/2004 | Lee |
| 2004/0172081 A1 | 9/2004 | Wang |
| 2004/0199059 A1 | 10/2004 | Brauker et al. |
| 2004/0199238 A1 | 10/2004 | Brown et al. |
| 2004/0230225 A1 | 11/2004 | Penner et al. |
| 2005/0015014 A1 | 1/2005 | Fonseca et al. |
| 2005/0056539 A1 | 3/2005 | Morgan et al. |
| 2005/0060186 A1 | 3/2005 | Blowers et al. |
| 2005/0065815 A1 | 3/2005 | Mazar et al. |
| 2005/0080346 A1 | 4/2005 | Gianchandani et al. |
| 2005/0102002 A1 | 5/2005 | Salo et al. |
| 2005/0124904 A1 | 6/2005 | Roteliuk |
| 2005/0137490 A1 | 6/2005 | Scheiner et al. |
| 2005/0149143 A1 | 7/2005 | Libbus et al. |
| 2005/0154321 A1 * | 7/2005 | Wolinsky et al. ............. 600/486 |
| 2005/0159639 A1 | 7/2005 | Skliar et al. |
| 2005/0159789 A1 | 7/2005 | Brockway et al. |
| 2005/0182330 A1 | 8/2005 | Brockway et al. |
| 2005/0187482 A1 | 8/2005 | O'Brien et al. |
| 2005/0192637 A1 | 9/2005 | Girouard et al. |
| 2005/0192844 A1 | 9/2005 | Esler et al. |
| 2005/0197585 A1 * | 9/2005 | Brockway et al. ............. 600/486 |
| 2005/0215887 A1 | 9/2005 | Ben-Haim et al. |
| 2005/0222631 A1 | 10/2005 | Dalal et al. |
| 2005/0231374 A1 | 10/2005 | Diem et al. |
| 2005/0242479 A1 | 11/2005 | Petisce et al. |
| 2005/0288727 A1 | 12/2005 | Penner |
| 2006/0009818 A1 | 1/2006 | Von Arx et al. |
| 2006/0031378 A1 | 2/2006 | Vallapureddy et al. |
| 2006/0058588 A1 | 3/2006 | Zdeblick |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142651 A1 | 6/2006 | Brister et al. |
| 2006/0167359 A1 | 7/2006 | Bennett et al. |
| 2006/0235323 A1 | 10/2006 | Hatib et al. |
| 2007/0043394 A1 | 2/2007 | Zhang et al. |
| 2007/0049977 A1 | 3/2007 | Von Arx et al. |
| 2007/0060959 A1 | 3/2007 | Salo et al. |
| 2007/0129765 A1 | 6/2007 | Gilkerson et al. |
| 2007/0142727 A1 * | 6/2007 | Zhang et al. ................... 600/486 |
| 2007/0142866 A1 | 6/2007 | Li et al. |
| 2007/0149890 A1 | 6/2007 | Li et al. |
| 2007/0161914 A1 | 7/2007 | Zdeblick et al. |
| 2007/0282381 A1 | 12/2007 | Li et al. |
| 2008/0015421 A1 | 1/2008 | Penner |
| 2008/0015651 A1 | 1/2008 | Ettori et al. |
| 2008/0021333 A1 | 1/2008 | Huelskamp |
| 2008/0021972 A1 | 1/2008 | Huelskamp et al. |
| 2008/0046037 A1 | 2/2008 | Haubrich et al. |
| 2008/0051843 A1 | 2/2008 | Li et al. |
| 2008/0058651 A1 | 3/2008 | Shen et al. |
| 2008/0071178 A1 | 3/2008 | Greenland et al. |
| 2008/0077440 A1 | 3/2008 | Doron |
| 2009/0201148 A1 | 8/2009 | Tran et al. |
| 2009/0204163 A1 | 8/2009 | Shuros et al. |
| 2010/0094144 A1 | 4/2010 | Doron |
| 2010/0125211 A1 | 5/2010 | Stahmann et al. |
| 2010/0222833 A1 | 9/2010 | Salo et al. |
| 2010/0324378 A1 | 12/2010 | Tran et al. |

FOREIGN PATENT DOCUMENTS

| | | |
|---|---|---|
| EP | 0928598 | 7/1999 |
| EP | 1266606 | 12/2002 |
| EP | 1169085 | 8/2004 |
| WO | WO83/03345 | 10/1983 |
| WO | WO95/03086 | 2/1995 |
| WO | WO95/27531 | 10/1995 |
| WO | WO97/01986 | 1/1997 |
| WO | WO 97/18856 | 5/1997 |
| WO | WO97/32519 | 9/1997 |
| WO | WO97/33513 | 9/1997 |
| WO | WO97/47236 | 12/1997 |
| WO | WO98/26716 | 6/1998 |
| WO | WO98/29030 | 7/1998 |

| | | |
|---|---|---|
| WO | WO99/17095 | 4/1999 |
| WO | WO99/26530 | 6/1999 |
| WO | WO99/34453 | 7/1999 |
| WO | WO99/47205 | 9/1999 |
| WO | WO99/55223 | 11/1999 |
| WO | WO99/55225 | 11/1999 |
| WO | WO99/59460 | 11/1999 |
| WO | WO99/66988 | 12/1999 |
| WO | WO00/16686 | 3/2000 |
| WO | WO00/58744 | 10/2000 |
| WO | WO01/28627 | 4/2001 |
| WO | WO01/56467 | 8/2001 |
| WO | WO01/74278 | 10/2001 |
| WO | WO02/03347 | 1/2002 |
| WO | WO02/32502 | 4/2002 |
| WO | WO03/002243 | 1/2003 |
| WO | WO03/096889 | 11/2003 |
| WO | WO2005/089638 | 9/2005 |
| WO | WO2005/118056 | 12/2005 |
| WO | WO2006/033812 | 3/2006 |
| WO | WO2006/034183 | 3/2006 |
| WO | 2006045073 A1 | 4/2006 |
| WO | 2006045074 A2 | 4/2006 |
| WO | 2006045075 A1 | 4/2006 |
| WO | 2006069215 A2 | 6/2006 |
| WO | WO2007/030474 | 3/2007 |
| WO | WO2007/047287 | 4/2007 |
| WO | WO2007/070794 | 6/2007 |
| WO | WO2007/099533 | 9/2007 |
| WO | WO2008/011570 | 1/2008 |
| WO | WO2008/011592 | 1/2008 |
| WO | WO2008/011593 | 1/2008 |
| WO | WO2008/154145 | 12/2008 |

OTHER PUBLICATIONS

International Search Report and Written Opinion of international application No. PCT/US2007/074021, mailed Feb. 25, 2008, 14 pp.
B. C. Penney et al., "Simplified electrode array for impedance cardiography," Medical & Biological Engineering & Computing, 1985, 23, p. 1-7.
B. Henderson et al., "Interaction of Photodynamic Therapy and Hyperthermia: Tumor Response and Cell Survival after Treatment of Mice in Vivo," Cancer Research, vol. 45, 6071 (Dec. 1985).
Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.
Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.
C. Hierold et al. (Germany, 1998) "Implantable Low Power Integrated Pressure Sensor System for Minimal Invasive Telemetric Patient Monitoring" IEEE, pp. 568-573.
Dipl.-Ing. Torsten Eggers et al. (Germany) "Implantable Telemetric Endosytem (ITES)" IMSAS Institut Fur Mikrosensoren-Aktuatoren Und-Systeme, 1998. 2 pp.
E R. Cosman et al. (Massachussetts, Apr. 1979) "A Telemetric Pressure Sensor for Ventricular Shunt Systems" Surgical Neurology vol. 11, No. 4, pp. 287-294.
Fink, Mathias, "Time Reversal of Ultrasonic Fields—Part I: Basic Principles", IEEE Transactions on Ultrasonics, Ferroelectrics, and Frequency Control, vol. 39, No. 5, Sep. 1992, pp. 555-566.
G.W.H. Schurink et al. (1998) "Late Endoleak After Endovascular Therapy for Abdominal Aortic Aneurysm" Eur. J. Vasc. Endovasc. Surg. vol. 17, pp. 448-450.
Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.
GH White et al. (1997) "Endoleak Following Endoluminal Repair of AAA: Management Options and Patient Outcomes", J. Endovasc Surg, pp. 1-45.
Graichen et al., "Patient Monitoring System for Load Measurement with Spinal Fixation Devices," Med. Eng. Phys. 18, (1996), pp. 167-174.
Haas et al., "Photodynamic Effects of Dyes on Bacteria," Published in Mutation Research, 1979, vol. 60, pp. 1-11.
Hashima et al., "Nonhomogenous Analysis of Epicardial Strain Distributions During Acute Myocardial Ischemia in the Dog," J Biomech, Jan. 26, 1993: 19-35.
Hetzer R. et al., 1998, Daily non-invasive rejection monitoring improves long-term survival in pediatric heart transplantation, Ann. Thorac. Surg. (66):1343-1349.
J.A. Parrish, "Photobiologic Consideration on Photoradiation Therapy," pp. 91-108, Porphyrin Photosensitization, Plenum Press, (1983).
K.E. Uhrich et al., "Synthesis and characterization of degradable poly(anhydride-co-imides)", Macromolecules, 1995, 28, 2184-93.
Karl E. Richard et al. (Germany, Jan. 1999) "First clinical results with a telemetric shunt-integrated ICP-sensor" Neurological Research vol. 21, pp. 117-120.
Labrousse and Satre, "Photodynamic Killing of Dictyostelium Discoideum Amoebae Mediated by 4',5'-Diiodoflurescin Isothiocyanate Dextran. A strategy for the isolation of Thermoconditional Endocytosis Mutants," published in Photochemistry and Photobiology, 1993, vol. 67, No. 3, pp. 531-537.
Mackay et al., "Bio-medical Telemetry: Sensing and Transmitting Biological Information from Animals and Man," John Wiley & Sons, Inc. New York (1970) pp. 244-245.
Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.
Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.
Prof. Dr. Johannes Zacheja et al. (Germany, Sep. 1996) "An Implantable Microsystem for Biomedical Applications" Micro System Technologies 96, pp. 717-722.
S.K. Gupta et al. (1999) "Use of a Piezoelectric Film Sensor for Monitoring Vascular Grafts", The American Journal of Surgery, vol. 160, pp. 182-186.
Strickberger, S. Adam et al., "Extracardiac Ablation of the Canine Atrioventricular Junction by Use of High-Intensity Focused Ultrasound", Circulation, Jul. 13, 1999; downloaded from circ.ahajournals.org at ACS/GUIDANT on Jan. 4, 2008, pp. 203-208.
T. Chuter et al. (Sweden, Jan. 1997) "Aneurysm Pressure Following Endovascular Exclusion" Eur. J. Vasc. Endovasc. Surg. vol. 13, pp. 85-87.
T.A. Cochran et al. (1990) "Aortic Aneurysm Abdominal", Current Therapy in Adult Medicine, Fourth Edition.
Wu, Francois et al., "Time Reversal of Ultrasonic Fields—Part II: Experimental Results", IEEE Transactions on Ultrasonics, Ferroelectrics, and Frequency Control, vol. 39, No. 5, Sep. 1992, pp. 567-578.
Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.
Cohen, T.J. et al., "A Hemodynamically Responsive Antitachycardia System. Development and Basis for Design in Humans", Circulation 1990, vol. 82, No. 2, pp. 394-406, XP002560584.
Blacher, Jacques et al., "Aortic Pulse Wave Velocity as a Member of Cardiovascular Risk in Hypertensive Patients", Hypertension May 1999;33;1111-1117.
Farzaneh-Far, Ramin et al., Usefulness of Noninvasive Estimate of Pulmonary Vascular Resistance to predict Mortality, Heart Failure, and Adverse Cardiovascular Events in Patients With Stable Coronary Artery Disease (from the Heart and Soul Study), The American Journal of Cardiology, vol. 101, Issue 6, Mar. 15, 2008, pp. 762-766.
El Gamal, M.I.H. et al., "Chronic Ventricular Pacing With Ventriculo-Atrial Conduction Versus Atrial Pacing in Three Patients With Symptomatic Sinus Bradycardia", PACE, vol. 4, Jan.-Feb. 1981, pp. 100-106.

Fujiki, Akira et al., "Pacemaker Syndrome Evaluated by Cardiopulmonary Exercise Testing", PACE, vol. 13, Oct. 1990, pp. 1236-1241.

Bourgeois, Maurice J. et al., "Continuous Determination of Beat-to-Beat Stroke Volume from Aortic pressure Pulses in the Dog", Circulation Research, vol. 39, pp. 15-24 (1976).

Rozenman, Yoseph et al., "Wireless Acoustic Communication With a Miniature Pressure Sensor in the Pulmonary Artery for Disease Surveillance and Therapy of Patients With Congestive Heart Failure", Journal of the American College of Cardiology, 49:7, 2007, pp. 784-789.

Wesseling, KH et al., "Computation of Aortic Flow From Pressure in Humans Using a Nonlinear, Three-Element Model", Journal of Applied Physiology, vol. 74, Issue 5, pp. 2566-2573 (1993).

* cited by examiner

MULTIPLE SENSOR DEPLOYMENT

CROSS-REFERENCE TO RELATED APPLICATIONS

This application claims priority to U.S. Provisional Patent Application Ser. No. 60/820,050, entitled "Multiple Sensor Deployment," and to U.S. Provisional Patent Application Ser. No. 60/820,059, entitled "System and Method for Addressing Implantable Devices," both of which were filed on Jul. 21, 2006, and are incorporated herein by reference in their entirety for all purposes.

TECHNICAL FIELD

The present invention related to sensors that are implantable within the human body. More specifically, the invention relates to devices and methods for implanting multiple sensors within the human body.

BACKGROUND

Medical sensors can be implanted into the human body to retrieve diagnostic data regarding certain bodily functions. For example, pressure sensors located within the vascular system of the body can measure blood pressure at various locations within the body. FIG. 1 illustrates a representative sensor assembly 2 having a sensor 4 and a compressible retention member 6 positioned within a blood vessel 8. The sensor 4 is a self-contained device, having its own power supply and communication circuitry for communicating data to a remote device. Sensors of this type can be implanted into the body by inserting a catheter into the body and moving the catheter through the cardiovascular system until the end of the catheter is positioned at the desired implant location. The sensor can then be fed through the catheter and positioned within the appropriate blood vessel.

Due to the nature of the human body, portions of the vascular system through which the catheter is navigated can have relatively acute radii, and thus the catheter may be required to make one or more turns within the body before reaching the desired implant location. Thus, any sensor that is fed through the body must be small enough to negotiate any turns in the catheter when it is positioned within the body. This size limitation impacts the size of the power supply contained within the sensor and correspondingly, impacts the life of the power supply and thus the amount of time that a sensor can function within the body. For example, a sensor may have a power supply with a rated life of 10 years under normal use, including periodic recharging. It is not desirable to replace sensors of this type within the body. Therefore, it is desirable to be able to extend the length of time that diagnostic data can be retrieved at a given site without requiring replacement of sensors. What is needed, then, is a way to measure diagnostic data at a given site for longer periods of time, given the constraints of size on diagnostic sensors.

SUMMARY

The invention is directed toward a method of measuring pressure within the human body. The method includes implanting a pressure sensing assembly into a human body. The sensing assembly includes a flexible structure capable of expanding when implanted and first and second sensor members each having self contained power supplies. The method includes performing periodic data collection events, including collecting a sensor data packet from at least one of the first and second members.

The invention is also directed toward a sensor assembly for implantation into a human body. The sensor assembly includes a flexible structure capable of expanding when implanted within the human body and first and second sensor members. The first sensor member includes a self-contained power supply, a sensing element and an integral communication device capable of communicating with a remote communication device. The sensor assembly is, in one aspect, part of a pressure sensing system implanted within a human body. The pressure sensing system includes a remote communication device implanted within the human body. In one aspect of the invention, the remote communication device is a pulse generator. The remote communication device is capable of broadcasting messages to the sensors. Broadcast messages include address data that is recognized by the intended sensor members.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
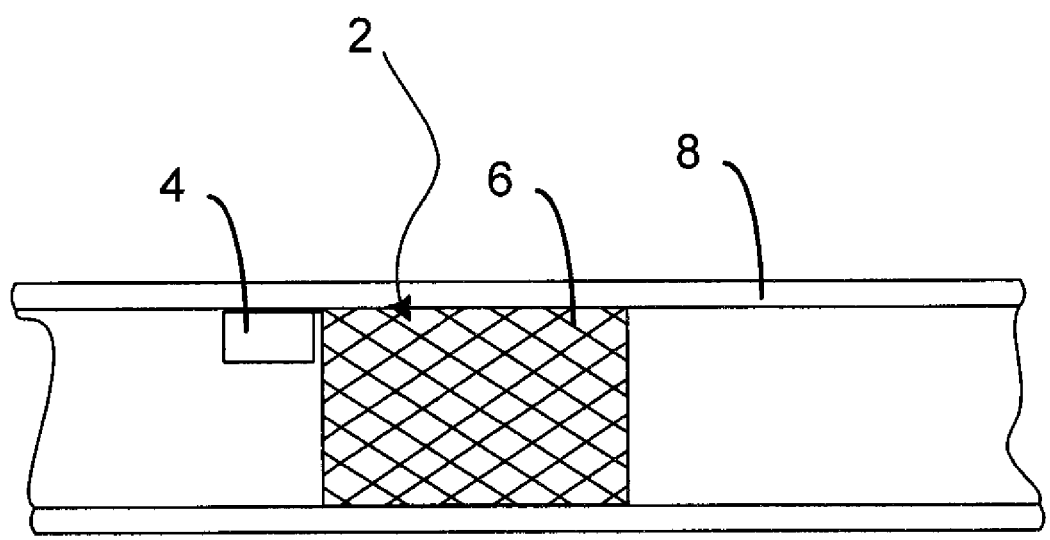
FIG. 1 is a cross-sectional fragmentary view of a cavity within the human body with a prior art implantable sensor assembly positioned therein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
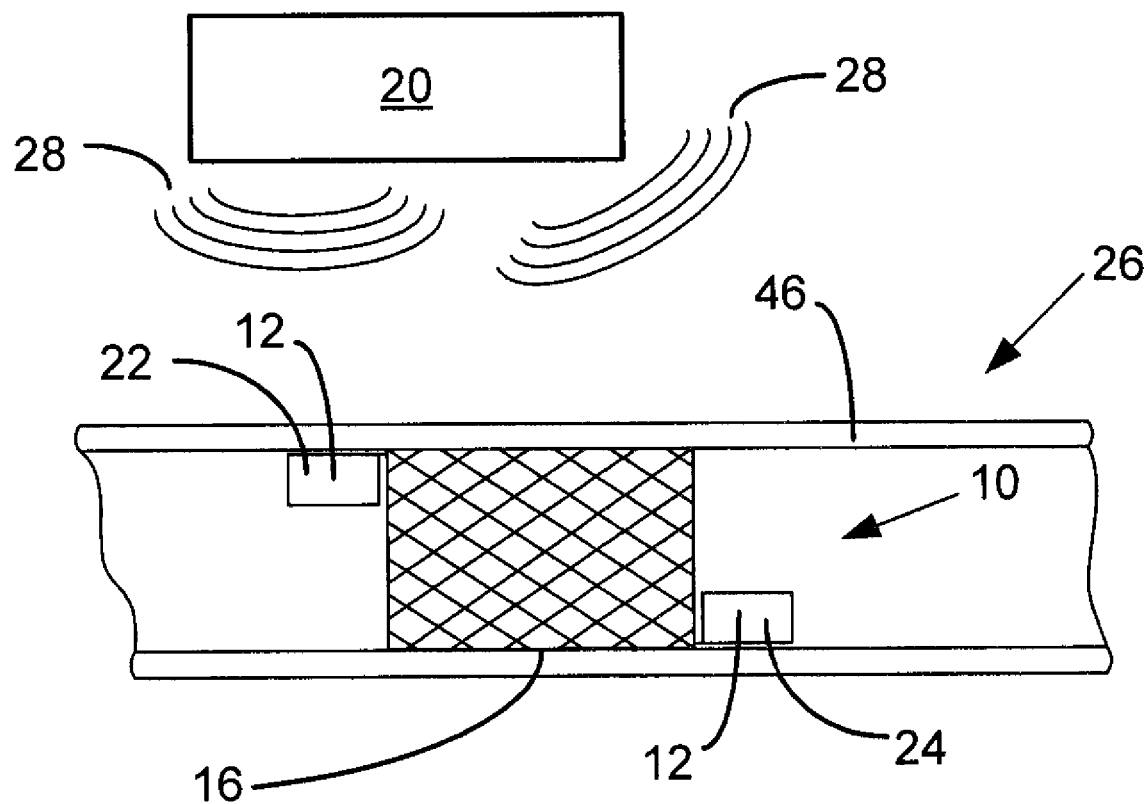
FIG. 2 illustrates an implantable multi-sensor assembly that can be used in relation to embodiments of the present invention.

FIG. 2 illustrates a sensor assembly 10 having a plurality of sensor members 12 each coupled to a compressible retention device 16 implanted into a blood vessel 26 of a human body according to one embodiment of the invention. The sensor assembly 10, as described below, includes two or more sensor members 12 and is capable of being implanted within the cardiovascular system of the human body to measure blood pressure at the implant location. The sensor assembly 10 is shown positioned within a blood vessel 26 within a human body. The compressible retention device 16 is expanded to contact the inner surface 46 of the blood vessel 26 to retain the sensor assembly 10 in its proper position. The compressible retention device 16 can be a stent, a strut, or other similar devices. Each of the sensor members 12 are coupled to the compressible retention device 16 by welding the sensor members 12 to the retention device 16 or by using other known coupling structures. The sensor assembly 10 is shown having two sensor members 12, although the sensor assembly can have any number of additional sensor members without departing from the scope of the invention. For example, the sensor assembly 10 could have a third sensor member (not shown) coupled to the compressible retention device 16.

When the sensor assembly 10 is implanted within the human body as shown in FIG. 2, the sensors 12 are capable of communicating with a remote communication device 20 via the communication link 28. The remote communication device 20, in one embodiment, is a pulse generator implanted within the human body. Alternatively, the remote communication device 20 can be any other device, either implanted within or externally located from the human body. In one embodiment, the communication link 28 between the sensors 12 and the communication device 20 is established using wireless acoustic communication. Alternatively, the communication link 28 can be established through inductive, radio frequency, or other communication technologies.

Figure 3:
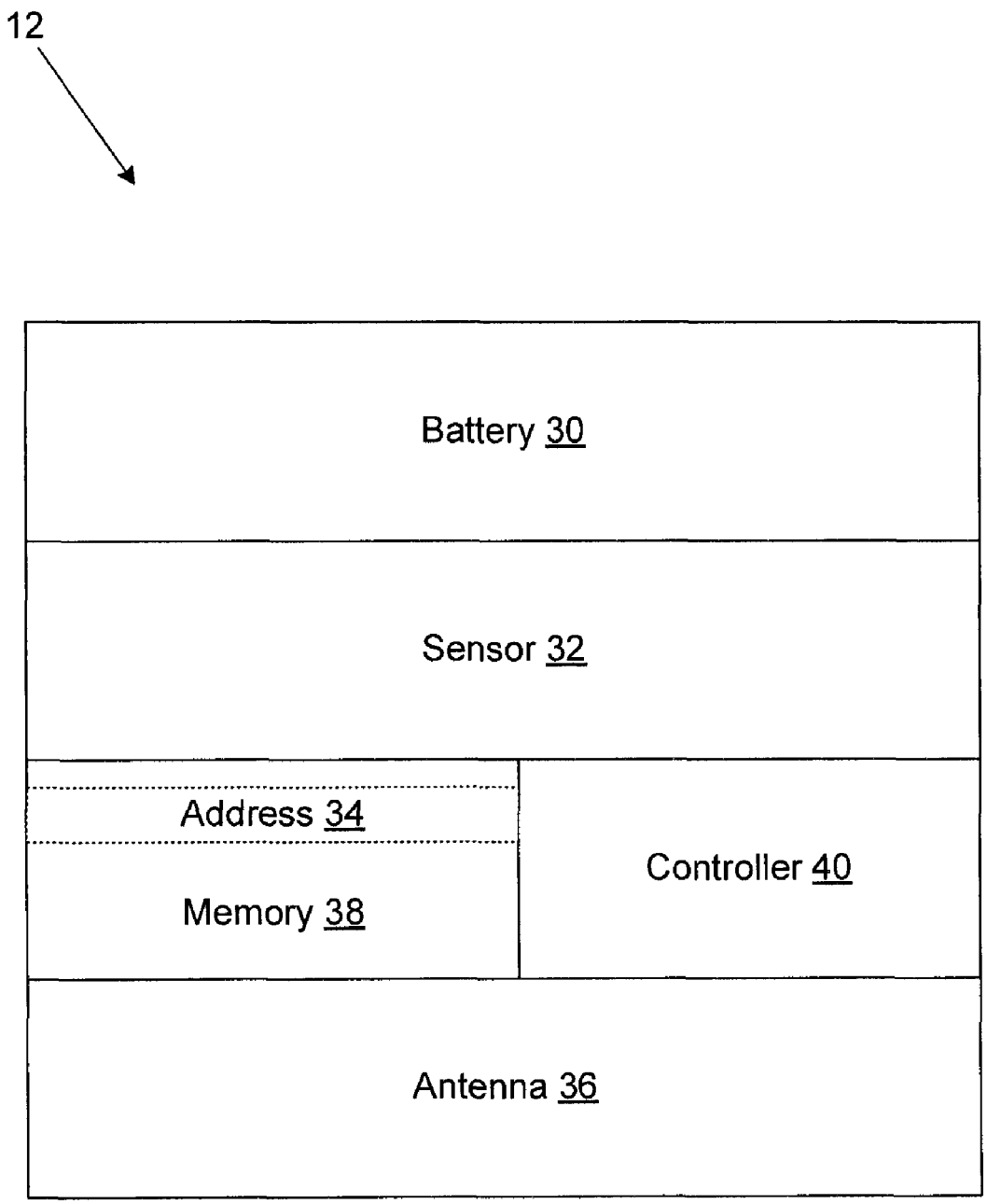
FIG. 3 is a functional block diagram of a sensor element of the multi-sensor assembly of FIG. 2.

Sensors 12 of the sensor assembly 10 are further identified as a first sensor member 22 and a second sensor member 24. For the purposes of this specification, the sensor members 12 of the sensor assembly 10 are referred to collectively or generically as sensor members 12, but individually and specifically as a first sensor member 22 and a second sensor member 24. FIG. 3 is a block diagram of the sensor member 12. The sensor member 12 includes a rechargeable power supply 30, a sensing element 32, a memory 38, including address data 34, a communication element 36, and a controller 40. The communication element 36 includes appropriate structure to communicate with the remote communication device 20 (FIG. 2) and can include one or more communication technologies of the types listed above and/or others. The power supply 30 can be a battery.

The memory 38 can be any type of memory known in the art. By way of example, but not limitation, the memory 38 can include random access memory (RAM) or read only memory (ROM). The memory 38 could include electrically erasable programmable ROM (EEPROM). Other types of memory may be known in the art that may be suitable for particular implementations. The controller 40 could be, without limitation, a microcontroller, a microprocessor, a digital signal processor, or an application specific integrated circuit (ASIC). The controller 40 may have registers for temporary storage of data or executable instructions, which may be read from memory 38.

The address data 34 provides identification within the sensor member 12 to allow the sensor member 12 to determine whether the sensor member 12 is the intended recipient of messages or data. Messages from the communication device 20 may be broadcast messages or targeted to particular sensor members. Targeted messages sent from the remote communication device 20 include an address associated with the intended sensor member 12. Each sensor member 12 processes messages that have an address that corresponds to its unique address. Thus, the remote communication device 20 is capable of directing a message to one or all of the sensor members 12. In one embodiment, the address data 34 is stored in reprogrammable or read only digital memory. It is anticipated that the first sensor member 22 and the second sensor member 24 can have the same or similar construction. However, the first sensor member 22 and the second sensor member 24 can include some differences and other features without departing from the scope of the invention.

The sensor element 32 detects a physiologic parameter, such as, but not limited to, pressure, and emits a signal corresponding to the detected parameter. In this respect, the sensor element 32 may be piezo or capacitive in nature, or any other appropriate technology for sensing a physiologic parameter of interest. Although embodiments described herein relate primarily to sensing of blood pressure, it will be understood by those of skill in the art that other types of physiologic parameters may be sensed, depending on the particular application. The sensor member 12 is typically housed in a housing composed of a bio-compatible material to facilitate implantation in the human body.

Figure 4:
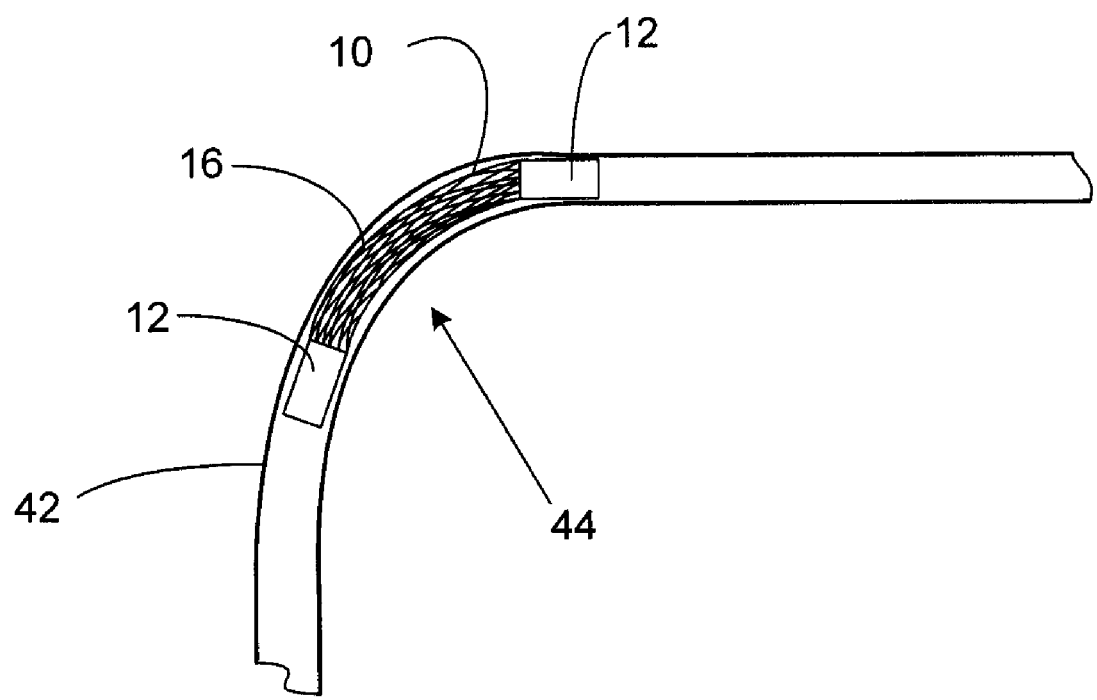
FIG. 4 is a cross-sectional view of the implantable multi-sensor assembly of FIG. 2 positioned at a radius within an insertion tool.

FIG. 4 illustrates a portion of an insertion tool 42 used to implant the sensor assembly 10 according to one embodiment of the invention. The insertion tool 42 can be a flexible catheter that is inserted into the vascular system of the human body and fed through to a desired implantation location within the human body. Once the insertion tool 42 is properly located within the human body, the sensor assembly 10 can be fed through the insertion tool 42 to the desired implantation location. When the sensor assembly 10 is loaded into the insertion tool 42, the compressible retention device 16 is compressed so that the sensor assembly 10 is capable of fitting within the insertion tool 42. As is shown in FIG. 4, the compressible retention member 16 is flexible enough to conform to a radius 44 and thus both of the sensor members 12 are able to pass though the radius. Once the sensor assembly 10 is fed through the insertion tool 42, it is located in the blood vessel 26 (FIG. 2). The compressible retention member 16 expands to engage the inner surface 46 of the blood vessel 26 to secure the sensor assembly 10 into position. Alternatively, the sensor assembly can be implanted in other portions of the human body, including, but not limited to, the esophagus and the air canal.

Figure 5:
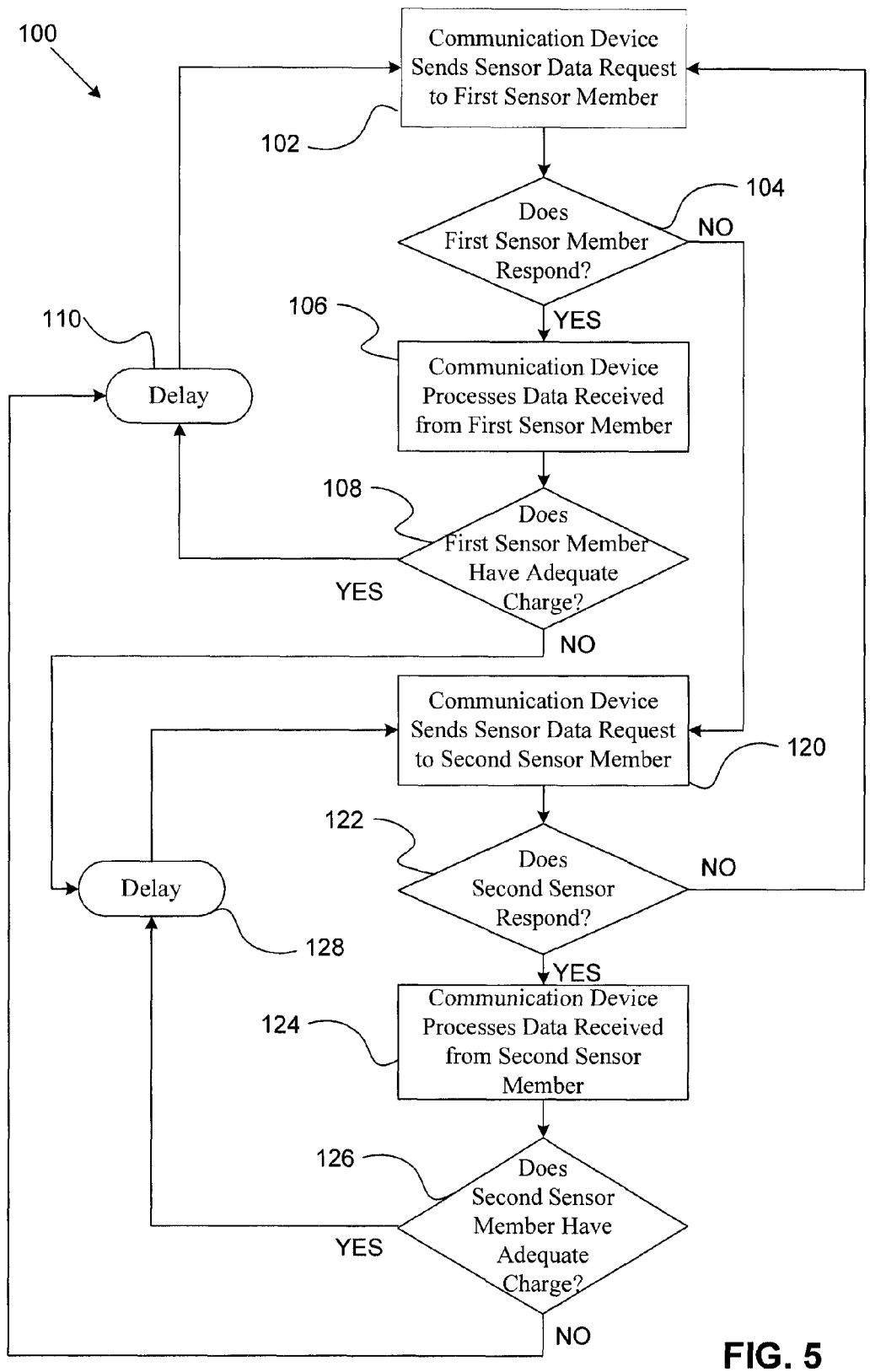
FIG. 5 is a flow diagram of a method of communication between the sensors of the multi-sensor assembly and a remote communication device according to one embodiment of the invention.

FIG. 5 is a functional flowchart 100 that illustrates a method of communicating sensor data packets between the remote communication device 20 (FIG. 2) and the sensor members 12 (FIG. 2) according to one embodiment of the invention. The remote communication device 20 and the sensor members 12 have a master/slave relationship such that the sensor members 12 rely on a communication from the remote communication device 20 before they perform any data collection and/or transmission. Therefore, it is the remote communication device 20 that determines what and when steps are taken in the communication method illustrated in flowchart 100. Prior to any request from the remote communication device 20, the sensor members 12 are in a power save state. It is to be understood that the description of the data collection method below describes the functional aspects of the method and that numerous implementations can be used to achieve the described functions. For example, communication protocols can be used to define the structure of messages sent between the remote communication device 20 and the sensor members 12. One particular implementation of the communication protocol between the remote communication device 20 and sensor members 12 is described in detail in related U.S. Pat. application Ser. No. 11/781,107, which was filed on the same day as this application and claims priority to U.S. Provisional Patent Application Ser. No. 60/820,059 and U.S. Provisional Patent Application Ser. No. 60/820,050, all of which are incorporated herein by reference in their entireties for all purposes.

Referring to block 102 of flowchart 100, the remote communication device 20 seeks to acquire a sensor data packet from the first sensor member 22. The remote communication device 20 initiates communication with the first sensor member 22 either at a predetermined time or in response to a request from an external communication device (not shown). The remote communication device 20 broadcasts a sensor data request message requesting sensor data from the first sensor member 22 (FIG. 2). The remote communication device 20 then waits a predetermined amount of time for the first sensor member 22 to respond. The data request message can request a single sensor data point, multiple sensor data points, or a continuous stream of data for a given period of time.

When a sensor data request message requesting sensor data from the first sensor member 22 is broadcast, all of the sensor members 12 receive the message and enter an identification state. When the sensor member(s) 12 is in an initialization state, the sensor member(s) 12 processes incoming communication data to determine whether the message is intended for that particular sensor. The sensor data request message from the remote communication device 20 includes an address. Each of the sensor members 12 compares the address in the sensor data request message to determine whether the address corresponds to that sensor member's address. If the sensor member(s) 12 determines that the addresses don't match, the sensor member(s) 12 ignores the message and returns to the power save state.

The sensor data request message of block 102 includes an address that corresponds to the unique address data 38 of the first sensor member 22. The first sensor member 22, recognizing that the address of the sensor data request message matches its unique address data 38 then enters into an active state in which the first sensor member 22 collects sensor data and transmits a sensor data packet back to the remote communication device 20. The sensor data packet, in one embodiment includes sensed data, such as pressure. In addition, the sensor data packet includes a power supply value that describes the charge level of its power supply. Once the first sensor member 22 has transmitted its data to the remote communication device 20, it returns to a power save state.

Referring to block 104, after sending the sensor data request message and waiting a predetermined length of time, if the remote communication device 20 has not received a sensor data packet from the first sensor member 22, the remote communication device 20 will request information from the second sensor member 24, as is illustrated in block 120 and described below. Before the remote communication device 20 sends a sensor data request message to the second sensor member 24, the remote communication device 20 may attempt more than once to collect information from the first sensor member 22. If, however, the remote communication device 20 does receive data from the first sensor member 22, the remote communication device 20 processes the sensor data packet received from the first sensor member 22 as illustrated in block 106 of flowchart 100.

The step of processing the sensor data packet can include storing the sensed data and/or power supply value, communicating the sensor data and/or power supply value to another remote device (not shown), using the sensor data and/or power supply value in calculations and/or algorithms, or any combination of the above. As shown in block 108, the remote communication device 20 next determines whether the first sensor member 22 has adequate charge left in its power supply 30 (FIG. 3). The power supply value is compared against a charge threshold value to determine whether the first sensor member 22 has sufficient charge remaining to continue collecting sensor data and to transmit it to the remote communication device 20. If the power supply value is greater than the threshold value, the first sensor member 22 has adequate charge remaining and the remote communication device waits (represented as a delay in block 110) either for a predetermined amount of time or for a request from another remote device (not shown) to go to block 102 and repeat the data collection cycle. If, however, the power supply value is lower than the threshold value, the first sensor member 22 has an inadequate charge left in its power supply, and the remote communication device 20 waits (represented as a delay in block 128) for either a predetermined amount of time or for an external request to go to request data from the second sensor member 24.

Block 120 represents the request for sensor data from the second sensor member 24. The remote communication device 20 sends a sensor data request message having an address that corresponds to the unique address 38 of the second sensor member 24. The remote communication device 20 then waits for the second sensor member 24 to respond. If the second sensor member 24 receives the sensor data request message, it enters an active state, collects sensor data and the power supply value, transmits a data packet back to the remote communication device 20, and returns to a power save state.

Referring to block 122, after sending the sensor data request message and waiting a predetermined length of time, if the remote communication device 20 has not received a sensor data packet from the second sensor member 24, the remote communication device 20 will request information from the first sensor member 22, as is illustrated in block 102 and described above. Before the remote communication device 20 sends a sensor data request message to the first sensor member 22, the remote communication device 20 may attempt more than once to collect a sensor data packet from the second sensor member 24. It should be noted that the remote communication device 20 requests sensor data from the second sensor member 24 only after either not receiving a response to a data request from the first sensor member 22 or due to a low charge condition on the first sensor member 22. However, because the power supply is rechargeable, it is entirely possible that the first sensor member 22 has been recharged and will be able to respond to a request for sensor data despite being unable to do so previously. If, however, the remote communication device 20 receives a sensor data packet from the second sensor member 24, the remote communication device processes the data packet as illustrated in block 124. The sensed data received from the second sensor member 24 is processed in a similar manner to that described above with respect to the first sensor member 22.

As illustrated in block 126, the remote communication device 20 next determines whether the second sensor member 24 has adequate charge left in its power supply 30. The power supply value of the second sensor member 24 is compared against the charge threshold value. If the power supply value is greater than the threshold value, the second sensor member 24 has adequate charge left in its power supply 30 and the remote communication device 20 waits (represented as a delay in block 128) either a predetermined amount of time, or for an external request to prompt the remote communication device to request data from the second sensor member 24 (as illustrated in block 120).

If, however, the power supply value is lower than the threshold value, the second sensor member 24 has an inadequate charge left in its power supply and the remote communication device 20 waits (represented as a delay in block 110) for a prompt to request sensor data from the first sensor member 22 (as illustrated in block 102). Alternatively, the remote communication device 20 may from time to time jump from block 128 to block 102 by issuing a sensor data request message with an address corresponding to the unique address 38 of the first sensor member 22 in attempt to request data from the first sensor member 22 even though the second sensor member 24 is working properly and has sufficient charge (not shown in flowchart 100). While flowchart 100 details the interaction between the remote communication device 20 and a sensor assembly 10 having two sensor members 12, other embodiments can include any number of sensor members 12. In those instances, the remote communication device 20 can move from one sensor to the next to get readings from a sensor with adequate charge in a way similar to that described here. Further, while flowchart 100 and the description above detail the transmission of a single sensor data packet transmission per sensor data request, a single data request could alternatively request a plurality of sensor data packets to provide readings over a period of time.

Figure 6:
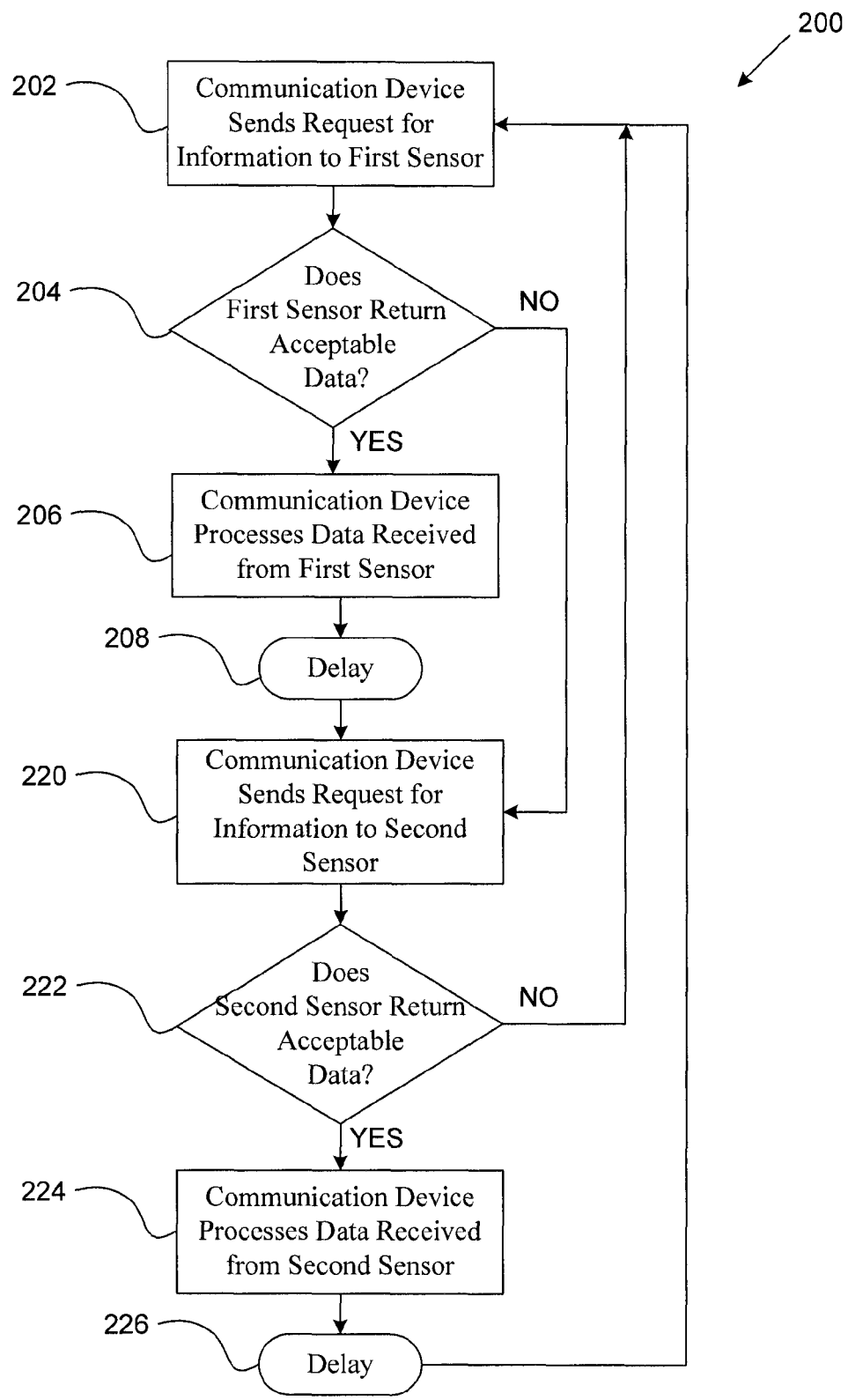
FIG. 6 is a flow diagram of a method of communication between the sensors of the multi-sensor assembly and a remote communication device according to another embodiment of the invention.

FIG. 6 is a functional flowchart 200 that illustrates a method of communication of sensor data between the remote communication device 20 and the sensor members 12 (shown in FIG. 2) according to another embodiment of the invention. In this embodiment, the remote communication device 20 alternates data collection between the first sensor member 22 and the second sensor member 24 (and any additional sensors) rather than collecting data from just one sensor until that sensor fails to respond or signals a low charge.

At block 202 of flowchart 200, the remote communication device 20 seeks to acquire sensor data from the first sensor member 22. The remote communication device 20 initiates communication with the first sensor member 22 by broadcasting a data request message having an address corresponding to the unique address 38 of the first sensor member 22 as is described above with respect to block 102 of flowchart 100. The first sensor member 22 responds as described above by providing a sensor data packet to the remote communication device 20 and then returns to a power save state.

Referring to block 204, after sending the sensor data request message and waiting a predetermined length of time, if the remote communication device 20 has not received a sensor data packet from the first sensor member 22, the remote communication device will request information from the second sensor member 24, as is illustrated in block 220 and described below. As in step 104 of flowchart 100, if the first sensor member 22 has not responded in a timely manner, the remote communication device 20 may attempt more than one request for information before attempting to communicate with the second sensor member 24.

If the remote communication device 20 receives timely data from the first sensor member 22, the remote communication device 20 processes the data at block 206. The step of processing the sensor data packet can include storing the sensed data and/or power supply value, communicating the sensed data and/or power supply value to another remote device (not shown), using the sensed data and/or power supply value in calculations and/or algorithms, or any combination of the above. After processing the sensor data packet, the remote communication device 20 waits, as represented in block 208, either for a predetermined amount of time or for a request from another remote device (not shown) to request data from the second sensor member 24.

Referring to block 220, the remote communication device 20 broadcasts a message requesting a sensor data packet from the second sensor member 24 similar to the procedure described above related to step 120. The first sensor member 22 responds by providing a sensor data packet to the remote communication device 20 as described above and then returns to a power save state.

Referring to block 222, after sending the sensor data request message and waiting a predetermined length of time, if the remote communication device 20 has not received a sensor data packet from the second sensor member 24, the remote communication device will request information from the first sensor member 22, as is illustrated in block 202 and described above. Before the remote communication device 20 sends a sensor data request message to the first sensor member 22, the remote communication device 20 may attempt more than once to collect a sensor data packet from the second sensor member 24. If neither the first sensor member 22, nor the second sensor member 24 is responding, the remote communication device 20 will not continuously shift between requesting sensor data packets from the first and second sensor members, 22, 24, but will wait a predetermined time before attempting to establish communication with the first sensor member 22 after it has been determined that neither sensor is responding to data requests. If, however, the remote communication device 20 receives data from the second sensor member 24, the remote communication device processes the data as illustrated in block 224. The data received from the second sensor member 24 is processed in a similar manner to that described above with respect to the first sensor member 22. After processing data received from the second sensor member 24, the remote communication device 20 waits, as represented by a delay in block 226, either for a predetermined amount of time or for a request from another remote device (not shown) to move to step 202 and request data from the first sensor member 22.

Figure 7:
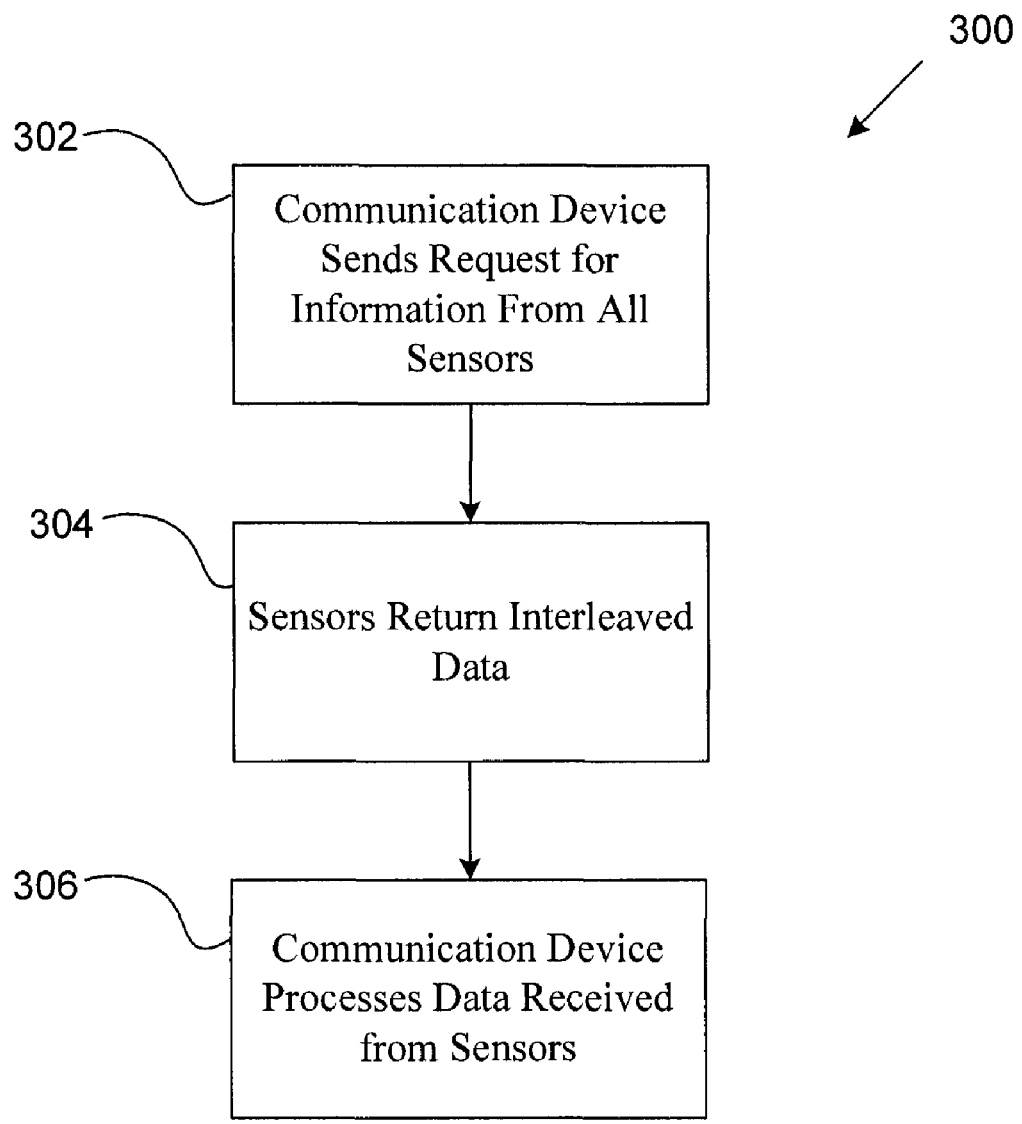
FIG. 7 is a flow diagram of a method of communication between the sensors of the multi-sensor assembly and a remote communication device according to yet another embodiment of the invention.

FIG. 7 is a functional flowchart 300 of a data collection method between the remote communication device 20 (FIG. 2) and the sensor members 12 (FIG. 2) according to another embodiment of the invention. In this embodiment, the remote communication device 20 requests a sensor data packet from each of the sensor members 12 simultaneously. A sensor data request can request data in different forms. For example, the sensor data request can specify that each of the sensors return a specified number of sensor data packets or the sensor members 12 return data values in a continuous stream of data for a given period of time. In response, the sensor members 12 transmit messages to the remote communications device 20. In some embodiments, sensor data values are transmitted sequentially in a specified order continuously from the time the remote communications device requests the sensor data until all of the data has been transmitted. In these and other embodiments, the data collection method may be performed in response to an external data request, or alternatively, it may be performed periodically.

Referring to block 302 of flowchart 300, prior to any communication between the remote communication device 20 and the sensor members 12, the sensor members are in a power save state. The remote communication device 20 requests a sensor data packet from each of the plurality of sensor members 12 by broadcasting a request for sensor data message including an address that corresponds to the global address 40 of each of the sensor members 12. In one embodiment, the message sent to request the sensor data from the sensor members 12 by the remote communication device 20 prescribes the order and for how long the sensor members 12 are to return information. For each sensor member 12, the remote communication device 20, in one embodiment, indicates how long after the request for sensor data a particular sensor should wait before making its first transmission, the delay between each subsequent transmission, and for how long the sensors are to return data after the request for sensor data.

As an example, a human body has two implanted sensor members 12 and it is desired that the two sensor members 12 transmit information for 10 seconds. Each sensor data packet transmission lasts 250 milliseconds. The first sensor member 22 will be instructed or will have stored within it to begin transmitting information at time t=0 and begin a transmission every 500 milliseconds. The second sensor member 24 will be instructed to begin transmitting information at time t=250 milliseconds and begin a transmission every 500 milliseconds thereafter. The request for data message may request continuous data for 10 seconds. Upon receipt of the request for data message, the first sensor member 22 begins transmission of its first sensor data packet at t=0 seconds. The second sensor member 24 begins transmission at t=250 milliseconds. The sensor members 12 then alternate sending packets every 250 milliseconds for 10 seconds so that the data returned from the sensor members 12 is interleaved. By staggering the transmissions, data collisions between two sensors attempting to transmit simultaneously are avoided. It should be understood that time t=0 may be some period of time after the receipt of the data message to allow time for the sensor to collect data.

The specific time intervals in the example above are not intended to be limiting, as any time interval may be used, depending upon the amount of data to be collected, the number of sensors implanted in the body, and the length of time required to transmit each message from one of the sensor members 12 to the remote communication device 20.

Alternatively, the remote communication device 20 can provide each sensor member 12 with specific information regarding its order prior to the request for data message sent to each of the sensor members individually, by transmitting a series of messages each of which has an address that corresponds to one of the unique addresses 38 (FIG. 3) of the sensor members 12. The information provided by the remote communication device 20 to each sensor member 12 includes when to begin transmitting packets after receiving the broadcast message requesting sensor data, how much time the sensor member 12 should wait before transmitting that information and how often to transmit the packets. Alternatively still, each sensor members 12 includes specific information stored within the sensor member regarding when to begin transmitting messages after receiving the broadcast message requesting sensor data packets and how often to transmit the messages, therefore not requiring any communication from the remote communication device 20 to set the order of transmission. Once communication is initiated by the remote communication device 20, the sensor members 12 are in an identification state. After receiving the request for sensor data message, the sensor members 12 are in an active state.

Referring to block 304, the sensor members 12 transmit sensor data to the remote communication device 20 using the interleaving pattern of staggering data transmissions described above. The information is sent for the period of time defined in the request for data. Once the sensor data has been transmitted to the remote communication device 20, the sensor members 12 return to a power save state. Referring to block 306, the data sent by the sensor members 12 and received by the remote communication device 20 is processed by the remote communication device 20. Processing data can include storing the sensor packet data within the remote communication device 20, communicating the sensor data to another remote device (not shown in FIG. 2), using the sensor packet data in calculations and/or algorithms, or any combination of the above.

By measuring pressure pulses at each sensor member 12, for example, in a pulmonary artery, given that the distance between the sensor members 12 is known, it is possible to calculate mass blood flow through the artery using the data from the pulses over time. A particular method for calculating blood flow rate is described in U.S. Pat. No. 6,277,078, issued Aug. 21, 2001, and entitled "System and Method for Monitoring a Parameter Associated With the Performance of a Heart," which is incorporated herein by reference for all purposes. In one embodiment, the data collection method illustrated in flowchart 300 and described above is initiated in response to an external request. Alternatively, the data collection method is performed periodically and is initiated after a specified period of time. While the remote communication device 20 may collect data periodically to measure mass blood flow, it need not use the data collection method described here exclusively. For example, the remote communication device 20 can use the method described in either the flowchart 100 or flowchart 200 primarily and intersperse the method described in flowchart 300 every 100 times data is collected or any other frequency.

In view of the foregoing, various embodiments are advantageous from several respects. For example, although optionally rechargeable, repeated recharging events and power drainage the power supplies can degrade and eventually be unable to maintain a charge. By having two or more sensors implanted in close proximity to one another, either of the sensors can be used to take readings, thereby reducing the overall usage of each sensor, and reducing the need for recharging events and, as a result, extending the life of sensors.

As another example, with the sensor assembly 10 according to various embodiments, it is possible to get sensors positioned more closely together where it would otherwise be difficult to implant two sensors close together without disturbing one or both of the sensors.

As another example, because the sensors of the assembly 10 are spaced apart at a known fixed distance according to some embodiments, it is possible to make calculations of mass blood flow by measuring the pulses as they pass each of the sensors as described above.

As a final example, because embodiments include multiple sensors (e.g., two), a redundant backup optionally exists for safety purposes.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of measuring blood pressure within a human body, comprising:
   implanting a pressure sensing assembly into a vessel near the heart in the human body, the sensor assembly including a flexible structure capable of expanding when implanted within the vessel, a first sensor member having a self contained electric power supply coupled to the flexible structure, and a second sensor member having a self contained electric power supply coupled to the flexible structure;

wirelessly transmitting a sensor data request message from a pulse generator implanted within the body to the first and second sensor members, the sensor data request message configured to prompt each of the first and second sensor members to transition from a power save state to an initialization state for a predetermined period of time for processing incoming communication data;

comparing an address in the sensor data request message against a unique address of the first and second sensor members and, upon receiving a matching address, selectively activating one of the first or second sensor members from the initialization state to an activation state in which a pressure sensor is activated for sensing pressure data; and performing periodic data collection events, including:
collecting a sensor data packet wirelessly transmitted to the pulse generator from the activated sensor member, the sensor data packet including a power supply value representing the charge level of the self-contained electric power supply of the activated sensor member;

comparing the power supply value of the activated sensor member against a threshold value;

wherein, if the activated sensor member has an adequate charge remaining, waiting for a predetermined period of time and then collecting another sensor data packet wirelessly transmitted to the pulse generator from the activated sensor member;

wherein, if the activated sensor member does not have an adequate charge remaining, waiting for a predetermined period of time and then collecting a sensor data packet wirelessly transmitted to the pulse generator from the other sensor member, the sensor data packet from the other sensor member including a power supply value representing the charge level of the self-contained electric power supply of the other sensor member; and periodically performing the steps of comparing the power supply value of an activated sensor member against a threshold value to determine a charge level and alternating the collecting of sensor data packets from either the first or second sensor member based at least in part on the charge level.

2. The method of claim 1, wherein the step of performing a data collection event includes collecting a plurality of sensor data packets from one of the first sensor member and the second sensor member.

3. The method of claim 1, wherein the step of performing a data collection event includes collecting a plurality of sensor data packets from each of the first sensor member and the second sensor member.

4. The method of claim 1, wherein the step of performing periodic data collection events includes:
providing a request for data from the pulse generator to the first sensor element;
transferring a sensor data packet from the first sensor member to the pulse generator in response to the request for data; and
processing the sensor data packet transferred to the pulse generator from the pressure sensing assembly in response to the request for data.

5. The method of claim 4, wherein the sensor data request message includes address information recognized by the first sensor member.

6. The method of claim 1, wherein the step of implanting a pressure sensing assembly includes:
inserting a first end of a hollow flexible insertion tool into the human body and feeding the insertion tool into the body so that the first end is positioned adjacent to a desired implantation site;
inserting the pressure sensing assembly into a second end of the insertion tool;
urging the pressure sensing assembly through the insertion tool until the assembly is seated at the desired implantation site; and
removing the insertion tool.

7. A method of measuring blood pressure within a human body, comprising:
implanting a pressure sensing assembly into a vessel near the heart in the human body, the sensor assembly including a flexible structure capable of expanding when implanted within the vessel, a first sensor member having a self contained electric power supply coupled to the flexible structure, and a second sensor member having a self contained electric power supply coupled to the flexible structure;

wirelessly transmitting a sensor data request message from an external device to the first and second sensor members, the sensor data request message configured to prompt each of the first and second sensor members to transition from a power save state to an initialization state for a predetermined period of time for processing incoming communication data;

comparing an address in the sensor data request message against a unique address of the first and second sensor members and, upon receiving a matching address, selectively activating one of the first or second sensor members from the initialization state to an activation state in which a pressure sensor is activated for sensing pressure data; and performing periodic data collection events, including:
collecting a sensor data packet wirelessly transmitted from the activated sensor member, the sensor data packet including a power supply value representing the charge level of the self-contained electric power supply of the activated sensor member;

comparing the power supply value of the activated sensor member against a threshold value;

wherein, if the activated sensor member has an adequate charge remaining, waiting for a predetermined period of time and then collecting another sensor data packet wirelessly transmitted to the external device from the activated sensor member;

wherein, if the activated sensor member does not have an adequate charge remaining, waiting for a predetermined period of time and then collecting a sensor data packet wirelessly transmitted to the external device from the other sensor member, the sensor data packet from the other sensor member including a power supply value representing the charge level of the self-contained electric power supply of the other sensor member; and periodically performing the steps of comparing the power supply value of an activated sensor member against a threshold value to determine a charge level and alternating the collecting of sensor data packets from either the first or second sensor member based at least in part on the charge level.

8. The method of claim 7, wherein the step of performing a data collection event includes collecting a plurality of sensor data packets from one of the first sensor member and the second sensor member.

9. The method of claim 7, wherein the step of performing a data collection event includes collecting a plurality of sensor data packets from each of the first sensor member and the second sensor member.

10. The method of claim 7, wherein the step of performing periodic data collection events includes:
providing a request for data from a remote communication device to the first sensor element;
transferring a sensor data packet from the first sensor member to the remote communication device in response to the request for data; and
processing the sensor data packet transferred to the remote communication device from the pressure sensing assembly in response to the request for data.

11. The method of claim 10, wherein the sensor data request message includes address information recognized by the first sensor member.

12. The method of claim 7, wherein the step of implanting a pressure sensing assembly includes:
inserting a first end of a hollow flexible insertion tool into the human body and feeding the insertion tool into the body so that the first end is positioned adjacent to a desired implantation site;
inserting the pressure sensing assembly into a second end of the insertion tool;
urging the pressure sensing assembly through the insertion tool until the assembly is seated at the desired implantation site; and
removing the insertion tool.

13. A method of measuring blood pressure within a human body, comprising:
implanting a pressure sensing assembly into a vessel near the heart in the human body, the sensor assembly including a flexible structure capable of expanding when implanted within the vessel, a first sensor member having a self contained electric power supply coupled to the flexible structure, and a second sensor member having a self contained electric power supply coupled to the flexible structure;
acoustically transmitting a sensor data request message from a remote communication device to the first and second sensor members, the sensor data request message configured to prompt each of the first and second sensor members to transition from a power save state to an initialization state for a predetermined period of time for processing incoming communication data;
comparing an address in the sensor data request message against a unique address of the first and second sensor members and, upon receiving a matching address, selectively activating one of the first or second sensor members from the initiation state to an active state in which a pressure sensor is activated for sensing pressure data; and
performing periodic data collection events, including:
collecting a sensor data packet acoustically transmitted to the remote communication device from the activated sensor member, the sensor data packet including sensed pressure data and a power supply value indicating the charge level of the self-contained electric power supply of the activated sensor member;
comparing the power supply value of the activated sensor member against a threshold value;
wherein, if the activated sensor member has an adequate charge remaining, waiting for a predetermined period of time and then collecting another sensor data packet wirelessly transmitted to the remote communication device from the activated sensor member;
wherein, if the activated sensor member does not have an adequate charge remaining, waiting for a predetermined period of time and then collecting a sensor data packet wirelessly transmitted to the remote communication device from the other sensor member, the sensor data packet from the other sensor member including a power supply value representing the charge level of the self-contained electric power supply of the other sensor member; and
periodically performing the steps of comparing the power supply value of an activated sensor member against a threshold value to determine a charge level and alternating the collecting of sensor data packets from either the first or second sensor member based at least in part on the charge level.

14. The method of claim 13, wherein the step of performing a data collection event includes collecting a plurality of sensor data packets from one of the first sensor member and the second sensor member.

15. The method of claim 13, wherein the step of performing a data collection event includes collecting a plurality of sensor data packets from each of the first sensor member and the second sensor member.

16. The method of claim 13, wherein the step of performing periodic data collection events includes
providing a request for data from the remote communication device to the first sensor element;
transferring a sensor data packet from the first sensor member to the remote communication device in response to the request for data; and
processing the sensor data packet transferred to the remote communication device from the pressure sensing assembly in response to the request for data.

17. The method of claim 16, wherein the sensor data request message includes address information recognized by the first sensor member.

18. The method of claim 13, wherein the step of implanting a pressure sensing assembly includes:
inserting a first end of a hollow flexible insertion tool into the human body and feeding the insertion tool into the body so that the first end is positioned adjacent to a desired implantation site;
inserting the pressure sensing assembly into a second end of the insertion tool;
urging the pressure sensing assembly through the insertion tool until the assembly is seated at the desired implantation site; and
removing the insertion tool.

19. The method of claim 13, wherein the remote communication device is configured to transmit the sensor data request message to each of the first and second sensor members in response to a request from an external device in communication with the remote communication device.

* * * * *